United States Patent [19]

Sumino et al.

[11] Patent Number: 4,593,000

[45] Date of Patent: Jun. 3, 1986

[54] METHOD OF PRODUCING GUANOSINE

[75] Inventors: Yasuhiro Sumino, Kobe; Koji Sonoi, Suita; Muneharu Doi, Takarazuka, all of Japan

[73] Assignee: Takeda Chemical Industries, Ltd., Osaka, Japan

[21] Appl. No.: 688,286

[22] Filed: Jan. 7, 1985

Related U.S. Application Data

[63] Continuation of Ser. No. 389,458, Jun. 17, 1982, abandoned.

[30] Foreign Application Priority Data

Jun. 22, 1981 [JP] Japan .................................. 56-97309

[51] Int. Cl.$^4$ .......................... C12P 19/40; C12N 1/00
[52] U.S. Cl. ........................................ 435/88; 435/243
[58] Field of Search ....................... 435/87, 88, 91, 92, 435/243, 244, 253, 802, 813, 832, 839, 840, 843

[56] References Cited

U.S. PATENT DOCUMENTS

| | | | |
|---|---|---|---|
| 2,822,319 | 2/1958 | Monod | 435/813 |
| 3,736,228 | 5/1973 | Nakayama et al. | 435/88 |
| 3,896,003 | 7/1975 | Ingestad et al. | 435/253 |
| 3,912,587 | 10/1975 | Enei et al. | 435/88 |
| 3,969,188 | 7/1976 | Enei et al. | |
| 4,306,026 | 12/1981 | Maslen et al. | 435/253 |

FOREIGN PATENT DOCUMENTS 1224893 3/1971 United Kingdom .

Primary Examiner—Esther M. Kepplinger
Attorney, Agent, or Firm—Wenderoth, Lind & Ponack

[57] ABSTRACT

A method of producing guanosine using an adenine-requiring microorganism, in which method the amount of the adenine-containing material to be added to the initial medium is restricted to not more than 50% of the required amount and, after the adenine-containing material added to the initial medium has been consumed almost completely, the remainder of the required amount is added intermittently or continuously.

2 Claims, No Drawings

METHOD OF PRODUCING GUANOSINE

This application is a continuation of now abandoned application Ser. No. 389,458, filed June 17, 1982, now abandoned.

This invention relates to a method of producing guanosine using a microorganism.

Guanosine is useful as a starting material in the production of 5'-guanylic acid which, as a seasoning, holds an important position in the food industry. Some methods are known for the production of guanosine by fermentation, for example a method using *Bacillus pumilus* or *Bacillus licheniformis* [Japanese Patent Publication (examined) No. 33392/1973] and a method using *Bacillus subtilis* [Japanese Patent Publication (examined) No. 2955/1980]. However, these known methods are not very advantagenous from the industrial viewpoint because the amount of guanosine accumulated in the fermentation broth can reach at most only 8–10 grams per liter.

The present inventors, as a result of intensive research work with the aim of increasing the accumulation of guanosine in the fermentation broth, have found that a significant increase in the yield of guanosine can be attained in the production of guanosine by growing an adenine-requiring, guanosine-producing microorganism, if the adenine-containing material, which is essential to the growth of the microorganism, is added in small portions intermittently or continuously in the course of incubation while taking the state of growth of the microorganism and other factors into consideration. Further research based on this finding has led to the present invention.

Thus, the invention provides a method of producing guanosine comprising growing an adenine-requiring, guanosine-producing microorganism in a medium and recovering guanosine thus produced and accumulated in the fermentation broth from said broth, which method is characterized in that the incubation is started in a medium containing not more than about 50% of the required quantity of an adenine-containing material and, after the adenine-containing material in the medium has been consumed almost completely, the incubation is continued with intermittent or continuous addition of the remaining quantity of said adenine-containing material.

The adenine-containing material to be used in practicing the invention includes, among others, adenine, adenosine, 5'-adenosine monophosphate, 3'-adenosine monophosphate, 5'-adenosine diphosphate, 5'-adenosine triphosphate, ribonucleic acid and deoxyribonucleic acid, and natural organic materials containing these, such as microbial cells, extracts therefrom, meat extracts and fish meat extracts, and further such adenine derivatives as adenylsuccinic acid.

In the prior art incubation of adenine-requiring microorganisms, the whole amount of the required adenine-containing material is added to the initial medium. In accordance with the present invention, the amount of the adenine-containing material to be added to the initial medium is restricted to not more than 50% of the required amount and, after the adenine-containing material added to the initial medium has been consumed almost completely, the remainder of the required amount is added intermittently or continuously.

The phrase "the required quantity of an adenine-containing material" as used herein means such a quantity of the adenine-containing material to be added to the medium that the production and accumulation of guanosine becomes maximal. Generally, this quantity, when expressed on the basis of adenine, is about 0.001 to 0.002 mole per liter of the medium although it depends on the microbial strain used and incubation conditions.

The phrase "after the adenine-containing material has been consumed almost completely" means that the amount of the adenine-containing material in the medium has become about 0.01 millimole or less per liter on basis of adenine at that point of time.

The mode of addition of the adenine-containing material in accordance with the present invention includes, among others, (1) intermittent or continuous addition, in equal portions or in time-dependent variable portions, of the required amount of the adenine-containing material according to a preliminarily specified time schedule, (2) intermittent or continuous addition of the adenine-containing material while varying the rate of addition depending on the change in the growth of the microorganism in the fermentation broth and (3) intermittent or continuous addition of the adenine-containing material in preliminarily specified doses depending on the state of growth of the microorganism as represented, for example, by the change in the dissolved oxygen concentration in the fermentation broth, the oxygen consumption by the fermentation broth or the heat produced in the fermentation broth, each detectable with a variety of sensors or detecting devices. Any of such addition modes is employable. Among them, the one comprising increasing the dose of the adenine-containing material as an exponential function of incubation time is most advantageous, particularly because it makes it possible to attain production and accumulation of a significantly large amount of guanosine in a short period of time. In this case, the dose of the adenine-containing material per unit time interval, F(t) (hereinafter called "feed rate"), at time t after commencement of the addition of the adenine-containing material, can be expressed by the following formula:

$$F(t) = F(O) \exp (Kt) \ (K \neq O)$$

where F(O) is the feed rate at the time of starting the addition and K is a constant (hereinafter called "specific feed rate"). In this mode, the amount of the adenine-containing material, $Ad_{TOTAL}$, added until time $t_{END}$ can be expressed by the following formula:

$$Ad_{TOTAL} = \frac{F(O)}{K} \{\exp(Kt_{END}) - 1\} + Ad_{IN}$$

where $Ad_{IN}$ is the quantity of the adenine-containing material added to the initial medium.

The time for starting the addition of the adenine-containing material, quantity of the adenine-containing material ($Ad_{TOTAL} - Ad_{IN} = Ad_{ADD}$), initial feed rate F(O) and specific feed rate K depend on the microbial strain and medium used, incubation conditions and other factors. Generally, however, the addition of the adenine-containing material should preferably be started when the growth of the microorganism has reached 0% to about 75%, more preferably about 5% to 50%, of the finally attainable growth level. The $Ad_{ADD}$ value is preferably about 25% to 100%, more preferably about 50% to 95%, of the amount required for the growth of said microorganism (generally, about 0.001 to 0.002 mole per liter on an adenine basis). F(O) is preferably about 0.1% to 50%, more preferably about 1% to 20%, of $Ad_{ADD}$ per unit time interval, and K is preferably about $0.01\ hr^{-1}$ to $5\ hr^{-1}$, more preferably about $0.05\ hr^{-1}$ to $0.2\ hr^{-1}$, and most preferably about 0.075 to $0.15\ hr^{-1}$.

The microorganism to be used in accordance with the present invention may be any adenine-requiring, quanosine-producing microorganism. Examples of such microorganisms are those belonging to the genus Bacillus, the genus Brevibacterium and the genus Corynebacterium, among others. The microorganisms belonging to the genus Bacillus include, among others, *Bacillus pumilus* and *Bacillus subtilis*, more specifically *Bacillus pumilus* No. 148-S-16 and *Bacillus subtilis* ATCC 19221. *Bacillus pumilus* No. 148-S-16 has been on deposit since June 4, 1981 at Fermentation Research Institute, Agency of Industrial Science and Technology, Ministry of International Trade and Industry, Japan (FRI) under the accession number FERM BP-6 in accordance with the provision of the Budapest Treaty, and on deposit since Jan. 11, 1967 at the Institute for Fermentation, Osaka (IFO), Japan under the accession number IFO 12483. *Bacillus subtilis* ATCC 19221 has also been on deposit since May 27, 1981 at IFO under the accession number IFO 14123. The ATCC number is the deposit number for the relevant strain deposited in the American Type Culture Collection (USA).

The above IFO 12483 strain is described in Japanese Patent Publication (examined) No. 33392/1973. The above ATCC 19221 strain is listed in The American Type Culture Collection Catalogue of Strains I, Fourteenth Edition, 1980.

For growing an appropriate microorganism in accordance with the present invention, a medium in which the microorganism can grow is used. Thus, for example, the carbon source to be added to the medium includes, among others, saccharides (e.g. starch, glucose, sucrose), mono- and polyhydric alcohols (e.g. glycerol, methanol, ethanol, sorbitol), fatty acids (e.g. acetic acid, propionic acid, stearic acid, oleic acid), fats and oils (e.g. soybean oil, olive oil, fish oil, whale oil, cottonseed oil, palm oil, lard), normal paraffins (e.g. nonane, decane, undecane, hexadecane, eicosane, pentacosane), and such hydrocarbons as kerosene, gas oil and heavy gas oil, and mixtures of these. The nitrogen source includes such organic nitrogen sources as peptone, soybean meal, corn steep liquor, yeasts and meat extract, and such inorganic nitrogen sources as the ammonium salt of sulfuric, nitric, hydrochloric or carbonic acid, gaseous ammonia, aqueous ammonia and urea; they are used alone or in combination. In addition, various inorganic salts necessary for the growth of said microorganism, such as calcium, potassium, sodium, magnesium, manganese, iron, copper and zinc salts of sulfuric, hydrochloric, carbonic, nitric, phosphoric, acetic and other acids, as well as amino acids, vitamins and other substances necessary for the growth of said microorganism may be selected for single or combined addition to the medium as the occasion may demand. Furthermore, antifoam, surface active and other agents, such as silicone oils and polyalkylene glycol ethers, may be added as necessary.

The incubation is carried out under aerobic conditions of shaking culture or submerged culture with aeration and stirring. The pH of the medium is generally selected within the range of about 5 to 8, preferably within the range of about 5.5 to 7.5. In case changes in the pH of the medium are observed during incubation, an aqueous solution or suspension of an alkali hydroxide (e.g. sodium hydroxide), calcium carbonate or ammonia, or gaseous ammonia, for instance, may be added during incubation in an adequate manner so as to adjust the pH to a value within the desired range. The incubation temperature may be selected so that it may be suited for the growth of the microorganism used. Generally, the incubation is carried out at about 20° C. to 60° C., preferably at about 25° C. to 45° C. The incubation time may be such that the maximum accumulation of guanosine can be attained during that time. Generally, the desired result can be obtained by incubation for about 24 to 144 hours.

The guanosine produced in the fermentation broth by the method of the present invention can be recovered by any of publicly known ordinary means, for example, chromatography using an ion exchange resin or activated carbon, precipitation, solvent extraction or other separation purification means, as employed alone or in combination.

The method of the present invention makes it possible to cause accumulation of guanosine in the fermentation broth in an amount approximately twice as much as the prior art methods by which the adenine-containing material is added to the medium all at once. Therefore, the use of the method of the present invention can result in an increase in the production of the desired product, namely guanosine, and moreover in ease of recovery of the guanosine owing to higher contents of guanosine in the fermentation broth. For these and other reasons, the method of the present invention is advantageous from the viewpoint of industrial production.

The following examples illustrate the present invention in more detail. In the examples, the percent (%) addition level for each additive added to the medium, unless otherwise stated, means the weight/volume percent (w/v, %) level.

EXAMPLE 1

*Bacillus pumilus* No. 148-S-16 (FERM BP-6, IFO 12483) grown on nutrient agar containing 100 ml/l of adenine was used for the inoculation of 20 ml of a sterilized seed medium each in five 200-ml Erlenmeyer flasks. The seed medium contained 4% glucose, 0.2% urea, 0.5% sodium L-glutamate, 0.2% magnesium sulfate (heptahydrate), 0.1% potassium chloride, 0.003% manganese sulfate (approximately tetrahydrate), 0.2% calcium chloride (dihydrate), 2% corn steep liquor, 0.25% ribonucleic acid, 0.03% histidine and 200 μg/l biotin. Then the incubation was performed with shaking at 37° C. for 18 hours.

The seed culture liquid (100 ml) was transplanted to a 5-liter jar fermenter containing 1 liter of a sterilized 22% glucose solution and 1 liter of a sterilized main fermentation medium containing 0.8% ammonium sulfate, 1.0% sodium L-glutamate, 0.4% magnesium sulfate (heptahydrate), 0.2% potassium chloride, 0.4% calcium chloride (dihydrate), 0.006% manganese sulfate (approximately tetrahydrate), 0.03% histidine, 400 μg/l biotin, 0.1% inosine, 5.0% corn steep liquor and 0.03% ribonucleic acid (about 10% of the required amount of the adenine-containing material), and the main fermentation was started at a temperature of 38° C., a stirring rate of 1,000 r.p.m. and an aeration rate of 0.6 V.V.M. For this medium, preliminary experiments had shown that the value of the product of the absorbance at the wavelength 590 nm (as measured as a represented value for indicating the growth level) and the number of times of dilution (said product hereinafter called "U.O.D.") was initially 4 and finally 32. Therefore, after 8 hours of incubation, when the U.O.D. value was 7.2 as a result of growth of the microorganism, the addition of a 10% solution of ribonucleic acid as the adenine-containing material was started at the initial feed rate $F(O)=0.003\%/hr$ and thereafter the addition was repeated at hourly intervals at the specific feed rate K as given in Table 1 until the total amount of ribonucleic acid added became 0.32% based on the medium volume. The incubation was thus conducted for 72 hours. The pH of the medium was maintained at 6.7 throughout the incubation by automatic addition of 25% aqueous ammonia. The fermentation broth thus obtained was analyzed for guanosine by high performance liquid chromatography. The results obtained are shown in Table 1.

ribonucleic acid added to the initial medium was varied as shown in Table 3. After the U.O.D. value reached the value shown in Table 3, the supplementary addition of ribonucleic acid was conducted at hourly intervals at $F(O)=0.003\%/hr$ and $K=0.1\ hr^{-1}$ until the total added amount of ribonucleic acid reached 0.3%. Guanosine assay was performed after 72 hours of incubation. The results obtained are shown in Table 3.

TABLE 3

|  | Ribonucleic acid concentration in initial medium (%) | Added amount of ribonucleic acid (%) | Time when addition was started U.O.D. | Time when addition was started Hours | Guanosine produced (g/l) |
| --- | --- | --- | --- | --- | --- |
| Example 3-1 | 0 | 0.30 | 4 | 0 | 12.3 |
| Example 3-2 | 0.015 | 0.285 | 5.5 | 6 | 14.2 |
| Example 3-3 | 0.03 | 0.27 | 7.5 | 8 | 16.6 |
| Example 3-4 | 0.06 | 0.24 | 10 | 10 | 16.5 |
| Example 3-5 | 0.15 | 0.15 | 20 | 14 | 10.8 |
| Comparative Example 3 | 0.27 | 0.03 | 30 | 18 | 9.0 |

TABLE 1

|  | Ribonucleic acid feed rate | Time when addition was finished (hours) | U.O.D. after 24 hours | Amount of guanosine produced (g/l) |
| --- | --- | --- | --- | --- |
| Comparative Example 1 | Added all at once (known method) |  |  | 8.0 |
| Example 1-1 | $K = 0.035\ hr^{-1}$ | 48 | 18 | 8.5 |
| Example 1-2 | $K = 0.050\ hr^{-1}$ | 42 | 20 | 10.4 |
| Example 1-3 | $K = 0.075\ hr^{-1}$ | 35 | 22 | 13.6 |
| Example 1-4 | $K = 0.10\ hr^{-1}$ | 31 | 25 | 15.4 |
| Example 1-5 | $K = 0.15\ hr^{-1}$ | 26 | 31 | 16.2 |
| Example 1-6 | $K = 0.20\ hr^{-1}$ | 23 | 33 | 12.0 |

EXAMPLE 2

Using Bacillus subtilis ATCC 19221 (IFO 14123) in place of Bacillus pumilus No. 148-S-16, the main fermentation was started under the same conditions as in Example 1. The U.O.D. value reached 7.5 in eight hours of incubation. Thereafter, ribonucleic acid was added at hourly intervals at the feed rate shown in Table 2 until the total added amount reached about 0.27 or 0.28%. Guanosine assay was performed after 72 hours of incubation. The results obtained are shown in Table 2.

TABLE 2

|  | Ribonucleic acid feed rate | Time when addition was finished (hours) | Guanosine produced (g/l) |
| --- | --- | --- | --- |
| Example 2-1 | 0.01%/hr | 34 | 13.8 |
| Example 2-2 | 0.02%/hr | 21 | 13.3 |
| Example 2-3 | 0.03%/hr | 16 | 9.5 |
| Comparative Example 2 | Added all at once |  | 7.2 |

EXAMPLE 3

The main fermentation was started using Bacillus pumilus No. 148-S-16 (FERM BP-6, IFO 12483) in the same manner as Example 1 except that the quantity of

EXAMPLE 4

Using a saccharified starch solution containing 196 g of glucose and 29 g of oligo saccharides per liter as a carbon source, the main fermentation was started using Bacillus pumilus No. 148-S-16 (FERM BP-6, IFO 12483) under the same conditions as in Example 1. After the U.O.D. value of 7.4 was attained by 8 hours of incubation, the supplementary addition of ribonucleic acid was performed at hourly intervals at the initial feed rate F(O) as shown in Table 4 and at the specific feed rate $K=0.1\ hr^{-1}$. The guanosine content after 72 hours of incubation was determined. The results obtained are shown in Table 4.

TABLE 4

|  | F(O) (%/hr) | Time when addition was finished (hours) | Amount of guanosine produced (g/l) |
| --- | --- | --- | --- |
| Example 4-1 | 0.003 | 31 | 15.9 |
| Example 4-2 | 0.01 | 21 | 16.7 |
| Example 4-3 | 0.03 | 14 | 14.3 |
| Example 4-4 | 0.1 | 10 | 9.6 |
| Comparative Example 4 | Added all at once |  | 8.1 |

EXAMPLE 5

Prior to starting the main fermentation using Bacillus pumilus No. 148-S-16 (FERM BP-6, IFO 12483) in the same manner as Example 1, 0.0001 mole per liter of the material shown in Table 5 was added to the initial medium as the adenine-containing material in place of ribonucleic acid. The fermentation was started and, when the U.O.D. value reached 7 or 8, the supplementary addition of said adenine-containing material was started at hourly intervals at the initial feed rate F(O)=0.0002 mole/l/hr and K=0.1 hr$^{-1}$ until the total added amount of the adenine-containing material reached 0.001 or 0.002 mole per liter. The fermentation broth after 72 hours of incubation was assayed for the guanosine content. The results obtained are shown in Table 5.

TABLE 5

| Example No. | Adenine-containing material | Time when addition was started | | Total added amount (mole/l) | Amount of quanosine produced (g/l) |
|---|---|---|---|---|---|
| | | hours | U.O.D. | | |
| 5-1 | Adenine | 6 | 7.2 | 0.001 | 14.7 |
| 5-2 | Adenine | 6 | 7.0 | 0.002 | 12.8 |
| 5-3 | Adenosine | 7 | 7.0 | 0.001 | 16.4 |
| 5-4 | Adenosine | 7 | 7.0 | 0.002 | 13.5 |
| 5-5 | 5'-Adenosine monophosphate | 8 | 7.8 | 0.001 | 15.4 |
| 5-6 | 5'-Adenosine monophosphate | 8 | 7.5 | 0.002 | 15.8 |

EXAMPLE 6

One liter of the fermentation broth obtained in Example 1 (K=0.1 hr$^{-1}$) with the guanosine content of 15.4 grams per liter was heated to 80° C. and centrifuged. The supernatant was cooled to 2° C. for precipitation of guanosine, giving 16.3 g of crude crystalline guanosine. The crude guanosine was suspended in 1 liter of water and the suspension was heated to 80° C. for dissolution and then cooled to 2° C. for recrystallization. There was thus obtained 13.3 g of crystalline guanosine.

What we claim is:

1. A method of producing guanosine which comprises growing a guanosine-producing microorganism, which requires adenine for its growth, in a medium and recovering guanosine thus produced and accumulated in the resultant fermentation broth from said broth, wherein incubation is conducted in a batch system and is started in a medium containing not more than about 50% of the quantity of an adenine-containing material required for maximal production and accumulation of the guanosine, and after the adenine-containing material in the medium has been almost completely consumed, the incubation is continued with intermittent or continuous addition of the remaining quantity of said adenine-containing material required for growth of the microorganism in accordance with the formula:

$$F(t)=F(O) \exp (Kt)$$

wherein F(t) is the dose of the adenine-containing material per unit time interval (feed rate), F(O) is the feed rate at the time of starting the addition, K is a constant (specific feed rate) and t is time after commencement of the addition of the adenine-containing material, wherein F(O) is about 0.1 to 50% and K is about 0.01 to 5 hr$^{-1}$.

2. A method according to claim 1, wherein the required quantity of the adenine-containing material is about 0.001 to 0.002 mole, on the basis of adenine, per liter of the medium.

* * * * *